United States Patent [19]

Mueller

[11] Patent Number: 5,039,795
[45] Date of Patent: Aug. 13, 1991

[54] PREPARATION OF BORONIC ACID DERIVATIVES

[75] Inventor: Richard H. Mueller, Ringoes, N.J.

[73] Assignee: E. R. Squibb & Sons, Inc., Princeton, N.J.

[21] Appl. No.: 369,390

[22] Filed: Jun. 21, 1989

[51] Int. Cl.$^5$ .............................. C07F 5/02; C07F 5/04
[52] U.S. Cl. .......................................... 534/14; 568/1; 568/6; 558/298; 549/213; 534/10
[58] Field of Search .................... 534/14; 568/1, 6, 7; 558/298; 549/213

[56] References Cited

U.S. PATENT DOCUMENTS

| | | | |
|---|---|---|---|
| 4,705,849 | 11/1987 | Nunn et al. | 534/14 |
| 4,795,821 | 1/1989 | Brown | 558/298 |
| 4,870,177 | 9/1989 | Brown | 558/298 X |

FOREIGN PATENT DOCUMENTS

| | | | |
|---|---|---|---|
| 814647 | 6/1959 | United Kingdom | 558/298 |
| 916189 | 1/1963 | United Kingdom | 558/298 |

OTHER PUBLICATIONS

Letsinger et al., *J. Org. Chem.*, vol. 18, (1953) pp. 895–897.
H. C. Brown et al., "Organoboranes: Improved Procedures for the Preparation of Boronic and Borinic Esters", *Organometallics*, vol. 5, pp. 2300–2304 (1986)

*Primary Examiner*—Robert L. Stoll
*Assistant Examiner*—John M. Covert
*Attorney, Agent, or Firm*—Theodore R. Furman, Jr.

[57] ABSTRACT

An improved process for preparation of compounds of the formula

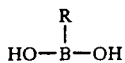

as disclosed. These compounds are useful as intermediates in the preparation of boronic acid adducts of technetium 99m dioxime complexes of the formula

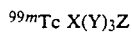

which are useful as imaging agents.

7 Claims, No Drawings

PREPARATION OF BORONIC ACID DERIVATIVES

BACKGROUND OF THE INVENTION

Compounds of the formula $$\text{HO}-\overset{\displaystyle R}{\underset{\displaystyle |}{B}}-\text{OH} \qquad \text{I}$$

or pharmaceutically acceptable salts thereof, wherein R is hydroxy, alkyl, alkenyl, cycloalkyl, cycloalkenyl, alkoxy, carboxyalkyl, carboxyalkenyl, hydroxyalkyl, hydroxyalkenyl, alkoxyalkyl, alkoxyalkenyl, haloalkyl, haloalkenyl, aryl, arylalkyl or $(R_1R_2N)$-alkyl, where $R_1$ and $R_2$ are each independently hydrogen alkyl or arylalkyl or taken together with the nitrogen to which they are attached form a 5- or 6-membered nitrogen-containing heterocycle are useful in the preparation of pharmaceutically important agents.

For example, U.S. Pat. No. 4,705,849, incorporated herein by reference, discloses boronic acid adducts of technetium-99m dioxime complexes having the formula $$^{99m}\text{Tc } X(Y)_3Z \qquad \text{II}$$

wherein
X is an anion;
Y is a vicinal dioxime having the formula $$\text{HO}-\text{N}=\overset{\displaystyle R'}{\underset{\displaystyle |}{C}}-\overset{\displaystyle R''}{\underset{\displaystyle |}{C}}=\text{N}-\text{OH}, \qquad (i)$$

wherein R' and R" are each independently hydrogen, halogen, alkyl, aryl, amino or a 5- or 6-membered nitrogen- or oxygen-containing heterocycle, or together R' and R" are $-(CR_4R_5)_n-$ wherein n is 3, 4, 5, or 6 and $R_4$ and $R_5$ are each independently hydrogen or alkyl; and Z is a boron derivative of the formula $$\text{B}-\text{R}. \qquad (ii)$$

These complexes are useful as imaging agents.

To prepare complexes of formula II, pertechnetate ion (in the form of a salt) is combined with a source of anion, a compound such as that of formula I and a dioxime of formula (i).

The pertechnetate ion can be obtained from commercially available technetium-99m parent-daughter generators; such technetium is in the +7 oxidation state. The generation of the pertechnetate ion using this type of generator is well known in the art and is described in more detail in U.S. Pat. No. 3,369,121 and 3,920,995. These generators are usually eluted with saline solution and the pertechnetate ion is obtained as the sodium salt.

The source of the anion moiety (X) can be water or it can be an acid or salt which dissociates to release an appropriate anion. Exemplary anionic moieties are hydroxyl, halide, isothiocyanato (N=C=S$^\ominus$) and thiocyanato (S—C=N$^\ominus$). The preferred anionic moieties are the halides, and chloride is the most preferred halide.

Brown et al., *J. Organometallics*, 5, 2300 (1986) describe a process for the preparation of methyl boronic acid which starts by reacting a compound of the formula $$\text{CH}_3\text{Li} \qquad (iii)$$

with a compound of the formula $$\begin{array}{c}(CH_3)_2\\|\\CH\\|\\O\\|\\B-O-CH-(CH_3)_2\\|\\O\\|\\CH\\|\\(CH_3)_2\end{array} \qquad (iv)$$

in ether to provide the complex $$[\text{CH}_3[(\text{CH}_3)_2\text{CHO}]_3 \text{ B}^-,\text{Li}^+]. \qquad (v)$$

Treatment of complex (v) with an equivalent of hydrogen chloride provides $$\begin{array}{c}(CH_3)_2\\|\\CH\\|\\O\\|\\CH_3B-O-CH-(CH_3)_2\end{array} \qquad (vi)$$

The byproduct LiCl is removed by a tedious decantation. Hydrolysis of (vi) is then accomplished by the addition of water to give methyl boronic acid and the byproduct $(CH_3)_2CHOH$. The reaction solvent is then removed by distillation followed by a tedious azeotropic distillation with acetone of the excess water and apparently also the $(CH_3)_2CHOH$. The desired methyl boronic acid then remains as a residue. Thus, any byproduct LiCl not removed in the decantation process and any $(CH_3)_2CHOH$ remaining from the distillation are present as impurities in the isolated methyl boronic acid. For the preparation of methyl boronic acid and similar compounds, i.e., compounds of formula I, especially on a manufacturing scale, an improved process would be a very useful addition to the art.

SUMMARY OF THE INVENTION

In accordance with the present invention, an improved process for preparation of compounds of the formula $$\text{HO}-\overset{\displaystyle R}{\underset{\displaystyle |}{B}}-\text{OH} \qquad \text{I}$$

or pharmaceutically acceptable salts thereof, is disclosed, wherein R is alkyl, alkenyl, cycloalkyl, cycloalkenyl, alkoxyalkyl, alkoxyalkenyl, aryl, arylalkyl or $(R_1R_2N)$-alkyl, where $R_1$ and $R_2$ are each independently alkyl or arylalkyl or taken together with the nitrogen to which they are attached form a 5- or 6-membered nitrogen containing heterocycle. The present process involves hydrolysis of a complex of the formula $$[R(R_3-O)_3B^\ominus,\text{Li}^\oplus] \qquad \text{III}$$

wherein $R_3$ is alkyl to provide a complex of the formula $$[R(OH)_3B^-,\text{Li}^+] \qquad \text{IV}$$

which is thereafter treated with an acid to provide compounds of formula I which are readily extracted in high yields with an organic solvent.

DETAILED DESCRIPTION OF THE INVENTION

The present invention provides a straightforward, high yield process for the preparation of compounds of formula I. The present process is therefore useful in preparation of various of the the compounds described in U.S. Pat. No. 4,705,849 having the formula $$^{99m}Tc\ X(Y)_3Z. \qquad II$$

The present process is particularly useful in the preparation of compounds of formula I wherein R is methyl, i.e., methyl boronic acid. This is a key intermediate in preparation of complexes of formula II wherein X is chloro, Y is cyclohexanedione dioxime and Z is B-R where R is methyl (i.e., the boronic acid adduct, 99mTc (chlorine)(1,2-cyclohexanedione-dioxane)$_3$ methyl boron or complexes where X is chloro, Y is dimethylglyoxime, Z is B-R where R is 2-methyl-1 propane (i.e., the 2-methyl-1 propane boronic acid adduct of chloro tris dimethylglyoxime technetium).

Listed below are definitions of the terms used to describe the complexes of this invention. These definitions apply to the terms as they are used throughout the specification (unless they are otherwise limited in specific instances) either individually or as part of a larger group.

The terms "alkyl" and "alkoxy" refer to both straight and branched chain groups. Those groups having 1 to 10 carbon atoms are preferred.

The term "alkenyl" refers to both straight and branched chain groups. Those groups having 2 to 10 carbon atoms are preferred.

The term "aryl", when used in the definition of R, refers to phenyl and substituted phenyl wherein the substituents can be any groups compatible with the generation of the lithium complexes or reagents of formula III, formula IV and formula V, such as primary, secondary or tertiary alkyl, dialkylaminoalkyl, alkoxy, or alkoxyalkyl.

The term "aryl", when used in the definitions of R', R", R$_1$ or R$_2$, refers to phenyl and phenyl substituted with primary, secondary or tertiary alkyl, haloalkyl, aminoalkyl, alkylaminoalkyl, dialkylaminoalkyl, alkoxy, alkoxyalkyl, halogen, amino, hydroxy, or formyl groups.

Preferred "cycloalkyl" and "cycloalkenyl" groups are those having 5, 6 or 7 carbon atoms. The terms include those groups substituted with alkyl, alkoxy, aryl, arylalkyl or (R$_1$R$_2$N)-alkyl groups.

The terms "halide", "halo" and "halogen" refer to fluorine, chlorine, bromine and iodine.

The expression "5 or 6-membered nitrogen containing heterocycle" refers to all 5 and 6-membered rings containing at least one nitrogen atom. Exemplary aliphatic groups are dehydro derivatives of a compound having a formula

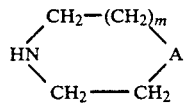

wherein m is 0 or 1 and A is O, N—R$_6$ or CH—R$_6$ wherein R$_6$ is alkyl, aryl or arylalkyl. Such groups include pyrrolidinyl, piperidinyl, morpholinyl, 4-alkylpiperazinyl, 4-alkylpiperidinyl, and 3-alkylpyrrolidinyl groups.

The expression "5 or 6-membered nitrogen or oxygen containing heterocycle" refers to all 5 and 6-membered rings containing at least one nitrogen or oxygen atom. Exemplary groups are those described above under the definition of the expression "5 or 6-membered nitrogen containing heterocycle". Additional exemplary groups are 1,4 -dioxanyl and furanyl.

To carry out the present process, a compound of the formula $$R\text{—}Li \qquad V$$

is reacted with a compound of the formula

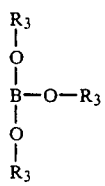

(wherein R$_3$ can be alkyl, and is preferably isopropyl, to provide a complex of the formula $$[R(R_3\text{—}O)_3B^\ominus, Li^\oplus]. \qquad III$$

Preferably the above reaction is carried out in diethyl ether cooled to between $-60°$ and $-80°$ C. As opposed to the prior art process, tri-ester complex III is thereafter hydrolyzed with water or an aqueous solution to provide $$[R(OH)_3B^\ominus, Li^\oplus]. \qquad IV$$

One distinct advantage of the present process is that complex IV can be readily isolated (as opposed to the di-ester complex of the prior art), i.e., via evaporation and the like, so as to remove any solvent and resultant R$_3$OH by-product while the desired intermediate of formula IV is in a non-volatile form. This provides for much easier isolation of the final product of formula I.

Thus, complex IV is concentrated to give a solid residue. The so-treated complex is thereafter treated with an acid to provide compounds of formula I which are readily extracted with an organic solvent using known techniques.

Preferably, the acid is an aqueous mineral acid, such as hydrochloric, sulfuric, phosphoric and the like, with hydrochloric acid being most preferred. The solvent can be any convenient organic solvent and preferably is a polar, low boiling point solvent, such as an ether (e.g., diethyl ether and the like) or methyl acetate.

The present invention is further illustrated by the following example.

EXAMPLE 504 ml (21.4 mole) of triisopropyl borate was added to 2200 ml of diethyl ether. This was cooled in a dry ice/acetone bath and 1530 ml 1.4 M (2.14 mole) methyl lithium in diethyl ether was added slowly over two hours. When the addition was complete, the cold bath was removed and the reaction was allowed to warm to room temperature over three hours. With vigorous stirring, 418 ml of water was added, slowly. The resulting mixture was stirred for 30 minutes The water layer was separated and the organic layer was extracted once with 110 ml water. The combined water layer was evaporated in vacuo at 50°. The resulting white, solid residue was stirred with 2300 ml diethyl ether and concentrated hydrochloric acid (201 ml, 2.40 mole) was added slowly until the pH of the aqueous layer stayed at 2.0. The aqueous layer was saturated with sodium chloride (~60 g) and the ether layer was separated. The aqueous layer was extracted with three 1000 ml portions of ether. The combined organic layer was dried over magnesium sulfate and evaporated at ~2 mm Hg/0°–5°. Final drying was accomplished with a vacuum pump at 20° for ten minutes. The resulting granular solid was suspended in 500 ml n-pentane and stirred for fifteen minutes. After filtration, the solid was washed with a little pentane and dried at 20 mm Hg/room temperature for 45 minutes to give 118 g (92 mole% yield) of the title compound.

What is claimed is:

1. A process for the preparation of compounds of the formula $$\begin{array}{c} R \\ | \\ HO-B-OH \end{array} \qquad I$$

wherein R is alkyl, alkenyl, cycloalkyl, cycloalkenyl, alkoxyalkyl, alkoxyalkenyl, aryl, arylalkyl or $(R_1R_2N)$-alkyl, where $R_1$ and $R_2$ are each independently alkyl or arylalkyl or taken together with the nitrogen to which they are attached form a 5- or 6-membered nitrogen containing heterocycle;

from a complex of the formula $$[R(R_3-O)_3B^{\ominus}, Li^{\oplus}] \qquad III$$

wherein $R_3$ is alkyl, which process comprises hydrolyzing the complex of formula III to provide a complex of the formula $$[R(OH)_3B^{\ominus}, Li^{\oplus}]; \text{ and} \qquad IV$$

treating the complex of the formula IV with an acid to provide compounds of formula I.

2. The process of claim 1 wherein the complex of formula III is hydrolyzed with water.

3. The process of claim 1 wherein said acid is an aqueous mineral acid.

4. The process of claim 3 wherein said aqueous mineral acid is selected from hydrochloric acid, sulfuric acid and phosphoric acid.

5. The process of claim 1 wherein, prior to said treatment with said acid, the complex of formula IV is extracted into an organic solvent.

6. The process of claim 5 wherein said solvent is selected from diethyl ether and methyl acetate.

7. In a process for preparing boronic acid adducts of the formula $$^{99m}Tc\ X(Y)_3Z$$

wherein
X is an anion;
Y is a vicinal dioxime having the formula $$\begin{array}{cc} R' & R'' \\ | & | \\ HO-N=C-C=N-OH \end{array} \qquad (i)$$

or a pharmaceutically acceptable salt thereof, and R' and R'' are each independently hydrogen, halogen, alkyl, aryl, amino or a 5 or 6-membered nitrogen or oxygen containing heterocycle, or together R' and R'' are $-(CR_4R_5)_n-$ wherein n is 3, 4, 5 or 6 and $R_4$ and $R_5$ are each independently hydrogen or alkyl;
Z is a boron derivative having the formula $$B-R$$

wherein R is alkyl, alkenyl, cycloalkyl, cycloalkenyl, alkoxyalkyl, alkoxyalkenyl, aryl, arylalkyl or $(R_1R_2N)$-alkyl, where $R_1$ and $R_2$ are each independently alkyl or arylalkyl or taken together with the nitrogen to which they are attached form a 5- or 5-membered nitrogen containing heterocycle; said process comprising the steps of combining a pertechnetate ion, with an anion source, a compound of the formula $$\begin{array}{c} R \\ | \\ HO-B-OH \end{array}$$

and a dioxane of formula (i);
the improvement wherein the compound of formula I is prepared by the process of claim 1.

* * * * *